United States Patent [19]
Ford et al.

[11] Patent Number: 5,459,122
[45] Date of Patent: Oct. 17, 1995

[54] AROMATIC OIL PESTICIDE ADJUVANT

[75] Inventors: Thomas J. Ford; Gilbert V. Chambers, both of Baytown, Tex.

[73] Assignee: Exxon Research & Engineering Co., Florham Park, N.J.

[21] Appl. No.: 233,831

[22] Filed: Apr. 26, 1994

Related U.S. Application Data

[62] Division of Ser. No. 985,400, Dec. 4, 1992, abandoned.

[51] Int. Cl.$^6$ ................................................ A01N 25/02
[52] U.S. Cl. ...................... 504/116; 71/DIG. 1; 514/770; 514/789
[58] Field of Search ................................ 504/206, 116; 71/DIG. 1; 514/770, 789

[56]         References Cited
U.S. PATENT DOCUMENTS

| | | | |
|---|---|---|---|
| 2,771,401 | 11/1956 | Shepherd | 196/28 |
| 3,022,245 | 2/1962 | Spars et al. | 208/26 |
| 3,089,841 | 5/1963 | Berkowitz et al. | 208/27 |
| 3,155,608 | 11/1964 | Hopper et al. | 208/251 |
| 3,175,970 | 3/1965 | Bercik et al. | 208/212 |
| 3,208,931 | 9/1965 | Wood | 208/27 |
| 3,227,609 | 1/1966 | Wilson et al. | 167/28 |
| 3,320,323 | 5/1967 | Lusskin et al. | 260/607 |
| 3,349,027 | 10/1967 | Carr et al. | 208/210 |
| 3,785,974 | 1/1974 | Scott | 252/28 |
| 3,884,797 | 5/1975 | Alley, Jr. et al. | 208/89 |
| 3,928,168 | 12/1975 | Mills et al. | 208/14 |
| 4,170,543 | 10/1979 | Lipscomb, II et al. | 208/14 |
| 4,175,278 | 11/1979 | Sato et al. | 361/315 |
| 4,499,187 | 2/1985 | Blackburn et al. | 435/34 |
| 4,584,129 | 4/1986 | Katayama | 252/570 |
| 4,801,373 | 1/1989 | Corman et al. | 208/210 |
| 4,966,728 | 10/1990 | Hazen | 71/DIG. 1 |

FOREIGN PATENT DOCUMENTS

| | | |
|---|---|---|
| 0071006 | 2/1983 | European Pat. Off. . |
| 1249850 | 10/1959 | France . |
| 2073228 | 1/1971 | France . |
| 56885 | 6/1965 | Germany . |
| 59354 | 12/1967 | Germany . |
| 1644962 | 4/1970 | Germany . |
| 72090 | 4/1970 | Germany . |
| 07511 | 1/1971 | Japan . |
| 46-3267 | 1/1971 | Japan . |
| 1024500 | 3/1966 | United Kingdom . |
| 1204220 | 2/1968 | United Kingdom . |
| 1476428 | 6/1977 | United Kingdom . |
| 2001339 | 1/1979 | United Kingdom . |
| 1546504 | 5/1979 | United Kingdom . |
| 0239310 | 9/1987 | United Kingdom . |

OTHER PUBLICATIONS

The Petroleum Handbook, Elsevier Science Publishing Co., New York, 1983, p. 458.
Orchex 796, For Agricultural Pest Control, Lubetext DG-2P, Exxon, printed in U.S.A. Feb. 24, 1989.

*Primary Examiner*—S. Mark Clardy
*Attorney, Agent, or Firm*—James H. Takemoto

[57]         ABSTRACT

An aromatic oil having an aniline point less than 120° F., a mutagenicity index based on The Modified Ames Test of less than 2.0, a benzene, naphthalene and methyl substituted benzenes and naphthalenes individual component concentrations less than 100 wppm, and a clay gel aromatics fraction content of at least 50 weight % based on aromatic oil, said aromatics fraction characterized in that it has a naphthene-benzenes and dinaphthenebenzenes content of at least 50 volume % based on aromatics fraction. The invention also relates to a process for preparing the aromatic oil which comprises the steps of selective solvent extraction, selective distillation and two-stage hydrotreating with removal of hydrogen sulfide and/or ammonia. The aromatic oils are useful in agricultural formulations due to their low environmental impacts.

1 Claim, 1 Drawing Sheet

5,459,122

AROMATIC OIL PESTICIDE ADJUVANT

This is a division, of application Ser. No. 985,400, filed Dec. 4, 1992, now abandoned.

BACKGROUND OF THE INVENTION

1. Field of the Invention

This invention relates to an improved aromatic oil and a process for preparing such aromatic oils. More particularly, the aromatic oils are prepared by a process which maximizes naphthene-benzenes and dinaphthenebenzenes content of the aromatic oil. Such aromatic oils are useful in environmentally sensitive applications such as agricultural formulations.

2. Description of the Related Art

Aromatic oils are used for a variety of purposes such as electric insulating oils, solvents and blending agents. Because of environmental considerations, the properties of aromatic oils are under increasing demands with regards to such matters as toxicity, carcinogenicity, and air and ground water contamination. Many commercially available aromatic oils have had their uses curtailed because of such environmental considerations.

Aromatic oils are made by a variety of processes depending on the final properties sought for the aromatic oil. Typically, such processes include hydrotreatment, reforming and fractionation or extraction to isolate an aromatic rich oil. Process oils having a relatively large mononuclear aromatic content and reduced polynuclear aromatic, sulfur and nitrogen contents can be prepared by hydrotreating a naphthenic feed in a two-stage hydrotreating process as described in U.S. Pat. No. 4,801,373.

It would be desirable to have an aromatic oil which maintains the favorable solvency properties of an aromatic oil while minimizing its potential environmental impacts.

SUMMARY OF INVENTION

The aromatic oil of this invention provides improved properties with regard to its impact on the environment, including low toxicity and carcinogenicity, low solubility in water, low vapor pressure, low odor, low aniline point and good solvency. The aromatic oil composition of this invention comprises an aromatic oil having an aniline point less than 120° F., a mutagenicity index based on the Modified Ames test of less than 2, a benzene, naphthalene, and methyl substituted benzene and naphthalene content each less than 100 wppm, and a clay gel aromatic fraction of at least 50 weight % based on oil, said aromatics fraction characterized in that it has a naphthenebenzenes and dinaphthenebenzenes content of at least 50 vol. %, based on the aromatic fraction.

Another embodiment of the invention relates to a process for preparing the aromatic oil set Forth above which comprises the steps of:

A. passing a naphthenic or paraffinic distillate stream into an extraction unit and controlling the extraction temperature, the solvent treat and the solvent water content to make an extract with an aromatics content of at least 60%;

B. passing the extract from the extraction unit to a distillation unit and controlling distillation to produce a distilled extract wherein the amount of material in the distilled extract having a boiling point range from about 450° to about 750° F. with a boiling point of 750° F. or greater, is no more than 5 weight %;

C. passing the distilled extract into a first hydrotreating stage maintained at a temperature of about 600° to about 750° F., and a hydrogen partial pressure of about 700 to about 1200 psig to convert at least a portion of the sulfur to hydrogen sulfide and the nitrogen to ammonia;

D. passing the hydrotreated extract From the first hydrotreating stage into an intermediate stripping stage wherein hydrogen sulfide and ammonia are removed;

E. passing the stripped hydrotreated extract from the intermediate stage into a second hydrotreating stage maintained at a temperature lower than that of the first stage and at a hydrogen partial pressure between about 700 and about 1200 psig;

F. passing the hydrotreated extract from the second hydrotreating stage into a final stripping stage wherein hydrogen sulfide and ammonia are removed;

G. monitoring the polynuclear aromatics content and/or the degree of saturation of the product exiting the final stripping stage; and, H. adjusting the temperature in the second hydrotreating stage to keep the polynuclear aromatics and/or the degree of saturation below a predetermined level.

Yet another embodiment relates to an agricultural pesticide or herbicide formulation which comprises an effective amount of pesticide or herbicide in a solvent or carrier fluid, said solvent or carrier fluid containing the aromatic oil of this invention as described above.

DETAILED DESCRIPTION OF THE INVENTION

Figure 1:
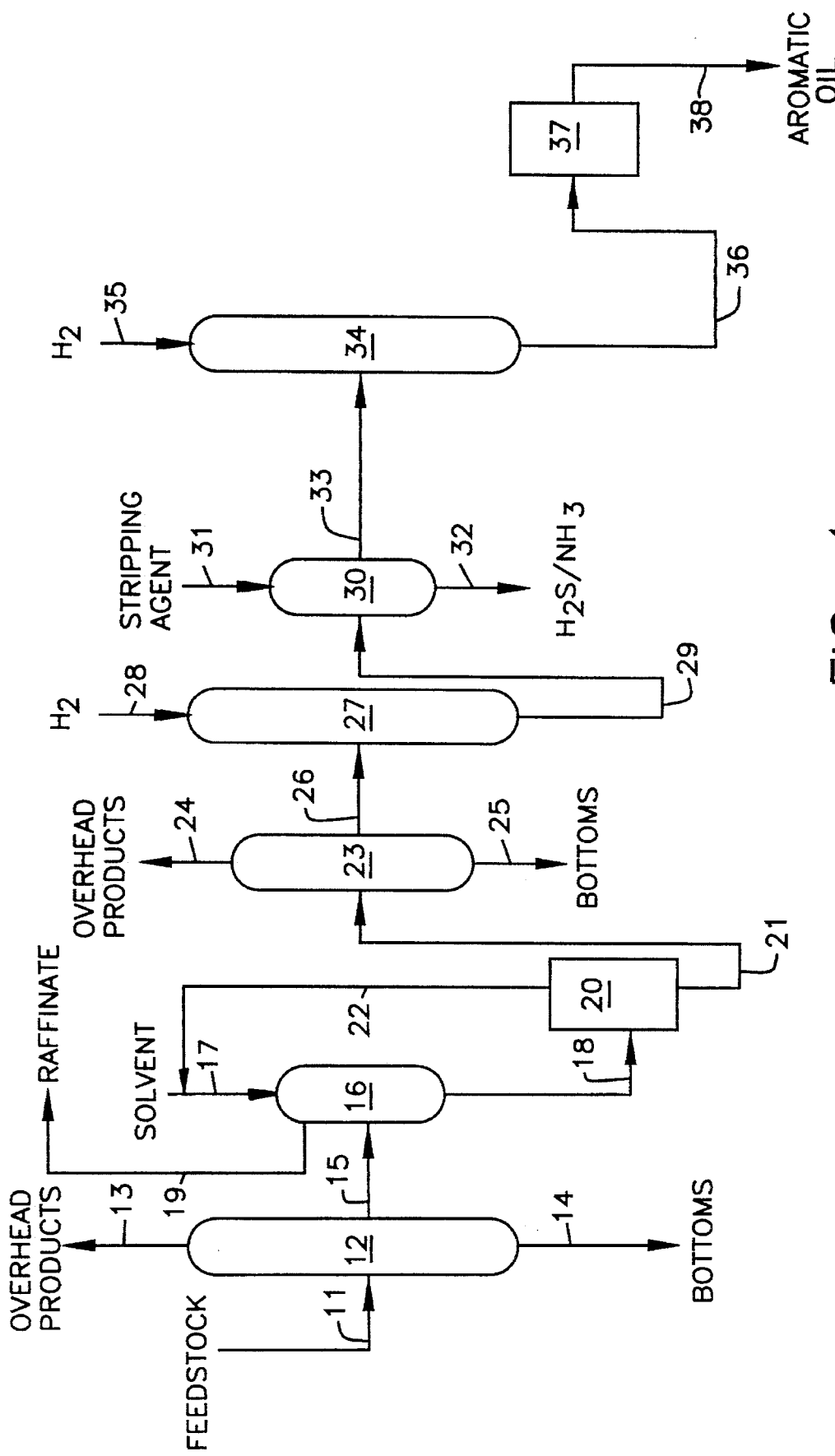
FIG. 1 is a drawing of a schematic flow diagram illustrating the process for manufacturing the aromatic oil according to the invention.

The process for manufacturing aromatic oils according to this invention is depicted in FIG. 1. An initial crude feedstock 11 is distilled in a pipestill 12. Volatile overheads and bottoms are taken off through lines 13 and 14, respectively. A naphthenic or paraffinic rich stream from the pipestill is fed through line 15 to a solvent extraction unit 16. Solvent is added through line 17 and a raffinate stream 19 and solvent extract stream 18 are removed from the extraction unit 16.

Conditions of extraction temperature, solvent treat ratio and solvent water content in the solvent extraction unit 16 are controlled to provide an aromatics rich solvent extract stream 18. Aromatic extraction solvents and extraction units are known in the art and include solvents such as n-methylpyrrolidone, phenol, n,n-dimethylformamide, dimethylsulfoxide, methylcarbonate, morpholine, furfural and the like, preferably n-methylpyrrolidone or phenol. Solvent oil treat ratios are from about 1:1 to about 3:1. The extraction solvent preferably contains water in the range from about 1 vol % to 20 vol %. Extraction units are preferably countercurrent type units. It is important to monitor the aromatics content of the extract phase and this can be accomplished by a clay gel measurement using ASTM D-2007. The aromatics rich solvent extract stream 18 is then solvent stripped in stripper unit 20 and solvent recycled through line 22. Solvent stripped stream 21 has a total aromatics content of at least 60% preferably at least 70%.

Aromatic rich stream 21 is fed to distillation unit 23 where a heart cut distillation takes place. Overheads 24 and bottoms 25 are removed from the distillation unit 23. The distillation based on ASTM D2887 is used to isolate a heart cut distillate which contains no more than 5 weight % of material with a boiling point of about 750° F., preferably a distillate cut containing no more than 5 weight % of material with a boiling point of about 700° F. The distillation heart cut has a boiling point range of from about 450° to about 750° F., preferably about 550° to about 700° F.

The heart cut distillate is then hydrotreated is a first hydrotreating zone 27. Hydrogen is added through 28 and maintained in zone 27 at a hydrogen partial pressure of about 700 to about 1200 psig. Temperatures in zone 27 are maintained at about 600° to about 750° F., preferably about 630° to about 720° F. The hydrotreating catalyst in zone 27 is not critical. However, the use of a catalyst having excessively high activity may result in an undesirably high increase in the total saturates level of the final product. Among the preferred catalysts are nickel-molybdenum sulfides, cobalt-molybdenum sulfides, cobalt-molybdenum-nickel sulfides, and nickel-tungsten sulfides. The hydrotreating occurs at a hydrogen treat rate of from about 350 to about 3000 SCF/B, preferably about 450 to 1500 SCF/B and the liquid hourly space velocity is from about 0.1 to about 4.0, preferably 0.25 to 2.0. The hydrotreating zone 27 converts a portion of sulfur present to $H_2S$ and nitrogen to $NH_3$.

The hydrotreating products from zone 27 are passed through 29 to an intermediate stripper 30. Stripping agent 31 added to the stripper to remove $H_2S$ and/or $NH_3$ is preferably steam, $CO_2$ or inert gas such as $N_2$. Saturated steam is especially preferred. Stripped $H_2S/NH_3$ is removed through 32 and stripped hydrotreated distillation cut fed through 33 to a second hydrotreating zone 34.

In the second hydrotreating zone 34, hydrotreating occurs using the catalysts set forth for zone 27 and $H_2$ added through 35 is maintained at similar partial pressure of about 700 to about 1200 psig. Other conditions of treat rates and space velocities are in the same range as zone 27. The temperature range in zone 34 is lower and is generally from about 400° F. to about 680° F., preferably 575° to 620° F.

The hydrotreated products from zone 34 are passed through line 36 to a monitoring zone 37 wherein the degree of saturation and polynuclear aromatics content are measured. A second stripper (not shown) equivalent to stripper 30 is incorporated between hydrotreating zone 34 and monitoring zone 37. This second stripper functions in the same manner as stripper 30. Monitoring of degree of saturation is typically determined by the aniline point utilizing ASTM Test D-611. A rise in aniline point is correlated to degree of saturation and is also a measure of the solubility properties. A rise in aniline point generally indicates that solubility properties have been reduced since for any given oil, degree of saturation is inversely related to solubility. Determination of polynuclear aromatic level in the product may be measured using ASTM D-2269-88. Using this test method, the product to be tested is extracted with a solvent such as dimethyl sulfoxide and the ultraviolet spectrum of extract measured. Generally, aromatics absorb light in the ultraviolet region of the spectrum. At given wavelengths characteristic of polynuclear aromatics, the absorbency of ultraviolet light is proportional to concentration. Preferred levels for four ring or larger polynuclear aromatics in the product aromatic oils is less than about 10 wppm.

Based on the data obtained from monitoring zone 37, the temperature in the second stage is adjusted for the particular feed rate, hydrogen partial pressure and gas treat rate in order to provide the desired control over the saturation process of aromatics in zone 34.

The aromatic oil 38 obtained from the process of the invention retains the favorable solvency properties of aromatic oils while reducing the environmental impact over other commercially available aromatic oils. The aniline point measured using ASTM D-611 is less than 120° F. thereby indicating favorable solubility properties. Next, subject aromatic oils have an aromatics fraction content of at least 50 weight % based on oil as measured by ASTM D-2007. This aromatics fraction from clay gel analysis is characterized by having a naphthenebenzene and dinaphthenebenzene content of at least 50 volume % based on the aromatics Fraction as measured using mass spectrometry based on ASTM D-3239. Naphthenebenzenes and dinaphthenebenzenes have the general formulae

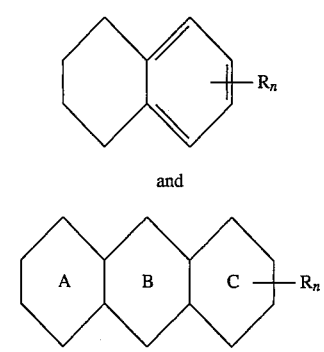

and where one of the rings A, B or C has a benzene structure, R is alkyl of from 1 to 10 carbon atoms and n is an integer from 1 to 6. The remainder of the aromatics fraction are mono- and di-aromatics which comprise one and two ring aromatics bearing at least one alkyl substituent typified by R as defined above. Another important feature is that the benzene, naphthalene and methyl substituted benzenes and naphthalenes concentrations are each less than 100 wppm.

Although the aromatic fractions described above have a naphthenebenzenes, dinaphthenebenzenes and mono- and di-aromatics (as defined above) content in excess of 90 volume %, the aromatic oils themselves have a mutagenicity index of less than 2 based on the Modified Ames Test as described in U.S. Pat. No. 4,499,187 which is incorporated herein by reference. The mutagenicity index is one measure of potential carcinogenicity and values less than 2 are generally taken to indicate a low probability of such carcinogenic behavior. These mutagenicity index values of less than 2 reflect the particular types of aromatics present in the aromatic oils according the invention. Typical commercial aromatic oils have naphthalene contents in excess of 100 wppm. These particular types of aromatic compounds plus other polynuclear aromatics may lead to environmental concerns when the use is environmentally sensitive, e.g., as carrier or solvent oils in pesticide formulations.

The subject aromatic oils are useful as carriers in pesticide and herbicide formulations. In addition to their favorable mutagenicity indices, they also possess low odor, low water solubility, low vapor pressure, flash point above 250° F., good color (Saybolt color 20) and are sprayable. Pesticide and herbicide formulations comprise an effective amount of pesticide or herbicide in the present aromatic oil as carrier or solvent. Such pesticides and herbicides are those which are known in the art. The oil itself can be employed as a non-selective contact herbicide for controlling undesirable weeds.

The aromatic oil and process for preparation are further illustrated in the following examples which include a preferred embodiment of the invention.

EXAMPLE 1

This example illustrates the preparation of samples of aromatic oils under the conditions set forth in Table 1. Numbers in the sample identification and treatment columns refer to FIG. 1. Feed is 60 Coastal Naphthenic Crude and catalyst in hydrotreating zones 27 and 34 is nickel-molybdenum sulfide.

EXAMPLE 2

This example compares the general properties of the aromatics oils from Example 1. The results are summarized in Table 2. Clay gel aromatics were analyzed using ASTM D-2007.

TABLE 1

| | | | | Treatment | | | |
|---|---|---|---|---|---|---|---|
| | | | | First Hydrotreat Zone (27) | | Second Hydrotreat Zone (34) | |
| Sample No. | Sample Identification Source | Extraction Solvent (6) | Distillation* Range (23) | Temp °F. | $H_2$ Pressure psig | Stripping Agent** | Temp °F. | $H_2$ Pressure psig |
| 1 | Commercial Aromatic Oil | N/A | N/A | N/A | N/A | N/A | N/A | N/A |
| 2 | Commercial Aromatic Oil | N/A | N/A | N/A | N/A | N/A | N/A | N/A |
| 3 | Sample from stream (21) - Raw extract | phenol | N/A | N/A | N/A | N/A | N/A | N/A |
| 4 | Sample from stream (26) - heart cut distillate extract | phenol | 567–689 | N/A | N/A | N/A | N/A | N/A |
| 5 | Sample from stream (21) which is directly hydrotreated in zones (27) and (34) | phenol | N/A | 671 | 800 | $N_2$ | 599 | 800 |
| 6 | Sample Run through process but at low $H_2$ pressures | phenol | 567–689 | 671 | 550 | $N_2$ | 599 | 550 |
| 7 | Sample according to the invention | phenol | 567–689 | 671 | 800 | $N_2$ | 599 | 800 |
| 8 | Sample according to the invention | phenol | 567–689 | 671 | 800 | $N_2$ | 599 | 800 |
| 9 | Sample from stream (15) which is directly hydrotreated in zones 27 and 34 | N/A | N/A | 675 | 550 | $N_2$ | 601 | 550 |
| 10 | Sample from stream (15) which is directly hydrotreated in zones 27 and 34 | N/A | N/A | 671 | 800 | $N_2$ | 596 | 800 |

*Distillation range is GCD 5–95% range.
**Same stripping agent is used in stripper 30 (FIG. 1) as well as in stripper following hydrotreat zone 34.

TABLE 2

| COMPARISON OF GENERAL COMPOSITIONAL FEATURES | | | | | | | | | | |
|---|---|---|---|---|---|---|---|---|---|---|
| | 1 | 2 | 3 | 4 | 5 | 6 | 7 | 8 | 9 | 10 |
| VOL % OFF* | | | | | | | | | | |
| 5 | 403 | 499 | 541 | 567 | 493 | 491 | 487 | 484 | 520 | 501 |
| 10 | 405 | 453 | 565 | 582 | 521 | 515 | 511 | 512 | 549 | 530 |
| 50 | 415 | 465 | 646 | 632 | 622 | 606 | 587 | 608 | 629 | 627 |
| 90 | 428 | 514 | 713 | 676 | 697 | 658 | 637 | 660 | 704 | 708 |
| 95 | 430 | 524 | 730 | 689 | 718 | 671 | 651 | 673 | 723 | 730 |
| Aniline point, °F. | 59 | 55 | 66 | 69 | 100 | 96 | 110 | 109 | 158 | 160 |
| Sulfur, wt % | — | <.001 | 2.18 | 1.75 | 0.148 | 0.103 | 0.012 | 0.017 | 0.027 | 0.012 |
| Surface Tension dynes/cm 73–75°F. | 29.85 | 37.55 | 32.85 | 32.25 | 31.70 | 31.4 | 30.55 | 31.35 | 30.15 | |
| COMPOSITION BY CLAY GEL ANALYSIS, WT % | | | | | | | | | | |
| Saturates | 0.4 | 0.2 | 25.3 | 28.1 | 36.4 | 36.8 | 46.3 | 43.7 | 65.7 | 66.9 |
| Aromatics | 99.6 | 99.8 | 70.7 | 69.3 | 62.2 | 62.4 | 53.2 | 56.3 | 34.1 | 32.9 |
| Polars | — | — | 4.00 | 2.58 | 1.41 | 0.79 | 0.42 | 0.01 | 0.22 | 0.18 |
| MODIFIED AMES TEST FOR MUTAGENICITY | | | | | | | | | | |
| Mutagenicity Index | — | — | 11.0 | 6.3 | 2.5 | 3.1 | 1.0 | 0.7 | 1.1 | 1.0 |
| Pass/Fail | NT | NT | Fail | Fail | Fail | Fail | Pass | Pass | Pass | Pass |

*Boiling Point By Gas Chromatographic Distillation (ASTM 2887), °F. at Vol. % indicated.

Samples 9 and 10 are aromatic oils produced according to the process of U.S. Pat. No. 4,801,373. These oils have aniline points greater than 120° F. and aromatics content less than 50 weight % as determined by clay gel analysis. Samples 3 to 6 have mutagenicity indices above 2.0 as determined by The Modified Ames Test.

EXAMPLE 3

Example 3 compares the types of aromatics present in the aromatics fraction from clay gel analysis. The volume % of various aromatic types were determined by mass spectrometry using ASTM D-3239. The results are summarized in Table 3.

zenes content in the aromatics fraction of greater than 50 volume %. This in turn provides an oil with both acceptable solvency and environmental/toxicological properties.

EXAMPLE 4

This example illustrates the selective reduction of certain target polynuclear aromatic compounds by comparing the naphthalene, 1-methyl naphthalene, 1,4-dimethyl naphthalene and pyrene in samples 3 and 8. The concentrations were determined using standard gas chromatography/mas spectrometry analysis using a Hewlett Packard (HP) Model 5890 gas chromatograph (GC) interfaced with a HP Model 5970 mass spectrometer. The GC column was a HP-5 with standard temperature programming of the GC oven (final tem-

TABLE 3

COMPARISON OF TYPES OF AROMATICS IN AROMATICS FRACTION BY MASS SPECTROMETRY (ASTM D3239), VOLUME %

| SAMPLE NO. | 1 | 2 | 3 | 4 | 5 | 6 | 7 | 8 | 9 | 10 |
|---|---|---|---|---|---|---|---|---|---|---|
| Monoaromatics | | | | | | | | | | |
| Alkylbenzenes | 89.3 | 9.1 | 9.8 | 7.6 | 16.0 | 12.7 | 16.2 | 18.1 | 20.1 | 16.5 |
| Naphthenebenzenes | 4.9 | 8.9 | 10.7 | 9.8 | 27.9 | 24.9 | 32.1 | 31.6 | 27.8 | 27.2 |
| Dinaphthenebenzenes | 0 | 0 | 15.6 | 16.4 | 27.6 | 28.2 | 30.5 | 31.0 | 25.5 | 27.7 |
| Diaromatics | | | | | | | | | | |
| Naphthalenes | 5.4 | 80.9 | 17.6 | 19.8 | 4.1 | 6.6 | 4.9 | 4.3 | 4.9 | 4.6 |
| Acenaphthenes, Dibenzofurans | 0 | 0.7 | 16.3 | 19.0 | 10.7 | 13.0 | 7.6 | 7.5 | 8.4 | 8.0 |
| Fluorenes | 0 | 0 | 10.7 | 10.2 | 5.7 | 6.4 | 3.2 | 2.9 | 4.8 | 4.4 |
| Triaromatics | | | | | | | | | | |
| Phenanthrenes | 0 | 0 | 5.8 | 4.7 | 1.7 | 1.5 | 0.6 | 0.7 | 1.7 | 1.2 |
| Naphthenephenanthrenes | 0 | 0 | 1.5 | 0.9 | 0.1 | 0.1 | 0 | 0 | 0.2 | 0.4 |
| Tetraromatics | | | | | | | | | | |
| Pyrenes | 0 | 0 | 1.7 | 1.4 | 0 | 0.4 | 0 | 0 | 0 | 0.9 |
| Chrysenes | 0 | 0 | 0.6 | 0.5 | 0.1 | 0.3 | 0 | 0 | 0.1 | 0.7 |
| Pentaaromatics | | | | | | | | | | |
| Perylenes | 0 | 0 | 0 | 0 | 0 | 0 | 0 | 0 | 0 | 0.1 |
| Dibenzanthracenes | 0 | 0 | 0 | 0 | 0 | 0 | 0 | 0 | 0 | 0 |
| Thiophenoaromatics | | | | | | | | | | |
| Benzothiophenes | 0 | 0.2 | 3.8 | 4.5 | 1.2 | 2.2 | 2.1 | 1.1 | 2.3 | 3.0 |
| Dibenzothiophenes | 0 | 0 | 5.7 | 5.2 | 4.6 | 3.8 | 2.7 | 2.7 | 3.2 | 4.3 |
| Naphthobenzothiophenes | 0 | 0 | 0 | 0 | 0 | 0 | 0 | 0 | 0 | 0.1 |
| Unidentified Aromatics | | | | | | | | | | |
| Class I Incl w/naphthenephenanthrenes | | | | | | | | | | |
| II | 0 | 0.1 | 0 | 0 | 0 | 0 | 0 | 0 | 0 | 0 |
| III | 0 | 0 | 0 | 0 | 0 | 0 | 0 | 0 | 0 | 0 |
| IV | 0.4 | 0.1 | 0 | 0 | 0 | 0 | 0 | 0 | 0.9 | 1.0 |
| V | 0 | 0.1 | 0 | 0 | 0 | 0 | 0 | 0 | 0 | 0 |
| VI | 0 | 0 | 0 | 0 | 0 | 0 | 0 | 0 | 0 | 0 |
| VII | 0 | 0 | 0 | 0 | 0 | 0 | 0 | 0 | 0 | 0 |

Sample 1 is a commercial aromatic oil which is almost 90% alkylbenzenes. Sample 2 is a different commercial aromatic oil which is about 81% naphthalenes. Both samples contain low levels of naphthenebenzenes and dinaphthenebenzenes in contrast to Samples 7 and 8 according to the invention. Samples 3–6 contain sufficient amounts of polynuclear aromatics to cause these oils to have mutagenicity indices greater than 2.0.

The aromatic oils of this invention, Samples 7 and 8, are prepared by a process which controls the aromatics content to, and degree of hydrogenation of polynuclear aromatics in hydrotreating zones 27 and 34 in FIG. 1. This control over feedstock quality and selective hydrogenation produces an aromatic oil with a naphthenebenzenes and dinaphthenebenperature 300° C.). Carrier gas was $H_2$ at 40 cm/sec. Sample injection was 3 μl. The Limit of Detection was confirmed using the following method.

A solution containing 1000 ug/ml of naphthalene, 1-methylnapnthalene, 1,4-dimethylnaphthalene, and pyrene in methylene chloride was gravimetrically prepared and calibration blends were subsequently prepared in methylene chloride at the 100 and 10 ug/ml levels by serial dilution of the 1000 ug/ml blend. These solutions were used to determine the retention times of each compound, the peak area/concentration for each compound type, and to calculate the limit of detection of the procedure towards each compound, defined as the concentration which produced a signal 4 times greater in height than the average peak to peak height of a 0.5 minute section of the baseline. The mass spectrometer was programmed to monitor the outlet of the gas chromatograph for the molecular ion of each compound at the compound's known retention time which was determined from the analysis of the calibration blends. The peak area of each molecular ion was integrated and the concentration calculated using the external standard approach. Results are given in Table 4.

TABLE 4

QUANTIFICATION OF PNA COMPOUNDS AGAINST KNOWN STANDARDS

Concentration in Weight ppm by GC - MS Analysis

| RT (min) | Naphthalene 9.841 | | 1-Methylnaphthalene 13.182 | | 1,4-Dimethylnaphthalene 16.423 | | Pyrene 31.704 | |
|---|---|---|---|---|---|---|---|---|
| | Area Counts | Concen | Area Counts | Concen | Area Counts | Concen | Area Counts | Concen |
| 20 ppm standard | 965 | 19 | 913 | 36 | 640 | 35 | 341 | 20 |
| Example 8, aroms | — | <10 ppm | 621 | 24 | 1220 | 66 | — | <10 ppm |
| Example 3, aroms | — | <10 ppm | 1355 | 53 | 23441 | 1282 | — | <10 ppm | where wt. ppm (mg/l) is x = (area x in sample)(concentration x in standard) / (area x in standard)

As shown in Table 4, concentrations of naphthalene, 1-methylnaphthalene, 1,4-dimethyl naphthalenes and pyrene are all less than 100 wppm in sample 8 according to the invention. This is further indicative of the selective hydrogenation of undesirable polynuclear aromatics.

EXAMPLE 5

This example illustrates the general phytotoxic properties of the composition of this invention compared to a material that is typically utilized as a solvent in the formulation of pesticides. Test materials were samples 2 and 7 from Example 1 and were sprayed over the tops of field plots containing two indicator plants at a total spray volume of 2-gallons per acre and 10-gallons per acre. Each emulsive solvent was added to the water at the equivalent of 0.125 gallons per acre (1 pint), 0.25 gallons per acre (1 quart) and 1.0 gallon per acre. This total spray volume of 2 and 10 gallons per acre represent simulations of aerial and tractor applications. Indicator plants were cotton and green beans. A phytotoxic evaluation was made one day after application. Each evaluation used a 0–10 scale where 0=None and 0.5 to 1.0=trace to slight and 10=severe. Two observers walked each plot. The ratings for three replicates are summarized in Table 5 which is a comparison of phytotoxicity properties with cotton and beans as plant indicators.

TABLE 5

| | Phytotoxicity Ratings** | | | | | | | |
|---|---|---|---|---|---|---|---|---|
| | Cotton*** | | | | Green Beans | | | |
| Test Material | No. 2 | | No. 7 | | No. 2 | | No. 7 | |
| Total Spray Volume G/A | 2 | 10 | 2 | 0 | 2 | 10 | 2 | 10 |
| Rate of Emulsive material* in total spray volume G/A | | | | | | | | |
| 0.125 | 0 | 0 | 1.7 | 0 | 0 | 0 | 0.3 | 0 |
| 0.25 | 0.7 | 0 | 1.7 | 0 | 0.3 | 0 | 0.7 | 0 |
| 1.0 | 1.7 | 1.7 | 3.3 | 3.7 | 1.7 | 1.0 | 2.7 | 2.0 |
| 0 (Non-treated plot) | 0 | | | | 0.3 | | | |

TABLE 5-continued

| | Phytotoxicity Ratings** | | | |
|---|---|---|---|---|
| | Cotton*** | | Green Beans | |
| Test Material | No. 2 | No. 7 | No. 2 | No. 7 |
| Total Spray Volume G/A | 2  10 | 2  0 | 2  10 | 2  10 |

*Test material, 93 wt %; emulsifer, 7 wt %, same emulsifiers with No. 2 and No. 7.
**Phytotoxicity evaluations: 0–10 scale where 0 = None, 0.5 to 1.0 trace to slight and 10 = severe.
***Application: April 6, 1992; cotton at 2 leaf stage, 2"–3" ht; beans at 6 leaf stage, 6"–8" ht.

What is claimed is:

1. An agricultural pesticide or herbicide formulation which comprises an effective amount of a pesticide or herbicide in a carrier or solvent fluid, said carrier or solvent fluid being an aromatic oil having an aniline point less than 120° F.; a mutagenicity index based on The Modified Ames Test of less than 2.0; benzene, naphthalene and methyl substituted benzenes and naphthalenes individual component concentrations of less than 100 wppm; and a clay gel aromatics fraction content of at least 50 weight % based on the aromatic oil, said aromatics fraction characterized in that it has a naphthenebenzenes and dinaphthenebenzenes content of at least 50 weight % based on the aromatics fraction, wherein said naphthenebenzenes and dinaphthenebenzenes have the formulas

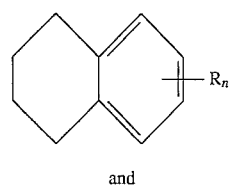

and

-continued
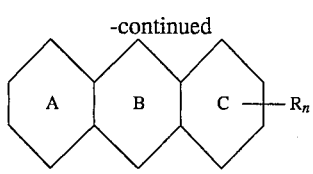
where one of rings A, B and C has a benzene structure, R is alkyl of from 1 to 10 carbon atoms and n is an integer from 1 to 6.
* * * * *